United States Patent
Salamone et al.

(10) Patent No.: US 8,263,749 B2
(45) Date of Patent: Sep. 11, 2012

(54) IMATINIB IMMUNOASSAY

(75) Inventors: Salvatore J. Salamone, Stockton, NJ (US); Jodi Blake Courtney, Doylestown, PA (US); Alexander Volkov, Allentown, PA (US)

(73) Assignee: Saladax Biomedical Inc., Bethlehem, PA (US)

( * ) Notice: Subject to any disclaimer, the term of this patent is extended or adjusted under 35 U.S.C. 154(b) by 0 days.

(21) Appl. No.: 13/287,467

(22) Filed: Nov. 2, 2011

(65) Prior Publication Data

US 2012/0045782 A1  Feb. 23, 2012

Related U.S. Application Data

(62) Division of application No. 12/543,699, filed on Aug. 19, 2009, now Pat. No. 8,076,097.

(51) Int. Cl.
  *C07K 16/00* (2006.01)
  *C07K 1/04* (2006.01)
(52) U.S. Cl. .......... 530/389.8; 530/388.9; 530/403; 424/175.1
(58) Field of Classification Search .............. None
  See application file for complete search history.

(56) References Cited

U.S. PATENT DOCUMENTS 7,300,768 B2 * 11/2007 Salamone et al. .......... 435/15

* cited by examiner

*Primary Examiner* — Shafiqul Haq

(57) ABSTRACT

Novel conjugates and immunogens derived from imatinib and monoclonal antibodies generated by these immunogens are useful in immunoassays for the quantification and monitoring of imatinib or its pharmacologically active salts in biological fluids.

9 Claims, No Drawings

IMATINIB IMMUNOASSAY

CROSS-REFERENCE TO RELATED APPLICATION

This Application is a divisional of Ser. No. 12/543,699, filed Aug. 19, 2009, now U.S. Pat. No. 8,076,097 entitled "Imatinib Immunoassay", which application is hereby incorporated by reference herein.

FIELD OF THE INVENTION

This invention relates to the field of immunoassays for determining the presence and/or quantifying the amount of imatinib or its pharmacologically active salts in human biological fluids in order to rapidly determine optimal drug concentrations during chemotherapy.

BACKGROUND OF THE INVENTION

Cancer is a term used to describe a group of malignancies that all share the common trait of developing when cells in a part of the body begin to grow out of control. Most cancers form as tumors, but can also manifest in the blood and circulate through other tissues where they grow. Cancer malignancies are most commonly treated with a combination of surgery, chemotherapy, and/or radiation therapy. The type of treatment used to treat a specific cancer depends upon several factors including the type of cancer malignancy and the stage during which it was diagnosed.

Imatinib has the following formula:

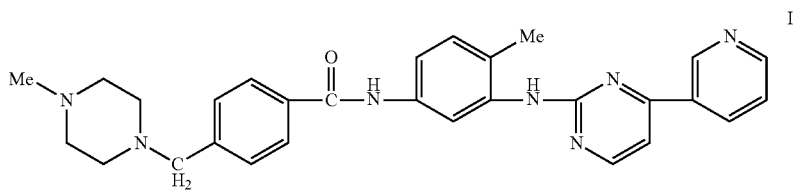

and its salts, particularly imatinib mesylate, are one of the more commonly used chemotherapeutic agents for treatment of Philadelphia chromosome positive chronic myeloid leukemia in blast phase, accelerated phase or chronic phase. (Gleevec package insert, Novartis Pharmaceuticals Corporation, July 2004).

Imatinib has been shown to have up to a 16 fold inter-patient variability in trough concentrations and that this variability can impact efficacy. (Picard et. al. Blood 2007: 109; 3496-3499, Larson et al. Blood 2008, 111: 4022-4028, Demetri et. al. J Clin Oncol 2009, 27: 3141-3147)

The preferred salt of imatinib is imatinib mesylate has the formula:

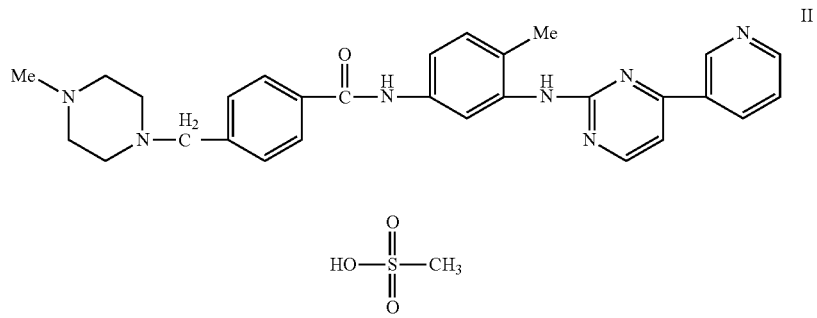

Since efficacy of imatinib is improved at higher trough levels and that the drug exhibits wide intra-patient pharmacokinetic variability monitoring concentrations of this drug in blood and adjusting to target levels would be of value in increasing efficacy and minimizing toxicity. The degree of intra- and inter-individual pharmacokinetic variability of imatinib and its salts has been reported to be 16 fold and is impacted by many factors, including:

Organ function
Genetic regulation
Disease state
Age
Drug-drug interaction
Time of drug ingestion
Compliance As a result of this variability, equal doses of the same drug in different individuals can result in dramatically different clinical outcomes. The effectiveness of the same dosage of imatinib or its salts varies significantly based upon individual drug clearance and the ultimate serum drug concentration in the patient. Therapeutic drug management would provide the clinician with insight on patient variation in drug administration. With therapeutic drug management, drug dosages could be individualized to the patient, and the chances of effectively treating the cancer without the unwanted side effects would be much higher.

In addition, therapeutic drug management of imatinib or its salts would serve as an excellent tool to ensure compliance (Henk, et al. Proc ASCO 2006, abst. 6083, Feng, et al. Proc ASCO 2006, abst. 6038) in administering chemotherapy with the actual prescribed dosage and achievement of the effective serum concentration levels. Routine therapeutic drug management of imatinib or its salts would require the availability of simple automated tests adaptable to general laboratory equipment. The use of liquid chromatography (LC)-tandem mass spectroscometry to determine the concentration of imatinib, imatinib salts or their chemotherapeutic metabolites in human blood and plasma has been described (Guetens, J Pharm Biomed Anal., 33(5):879-89 2003; Bakhtiar, J Chromatrography B, 768(2):325-340, 2002; Titier, Ther. Drug. Monit., (27)5:634-640, 2005). A LC method to determine the purity of imatinib, imatinib salts or their chemotherapeutic metabolites (Vivekanand, J Pharm Biomed Anal., 28(6):1183-94, 2002) has also been developed but was not used to determine levels in biological fluids. These methods are labor intensive, use expensive equipment and are not amenable to routine clinical laboratory use. An enzymatic assay for measuring imatinib has been developed set forth in U.S. Pat. No. 7,300,768. However there exists no simple immunoassay for determining the presence or quantifying the amount of imatinib in human biological fluids of patients treated with this chemotherapeutic agent.

As seen from the foregoing, there are no immunoassays for determining the presence and/or quantifying the amount of imatinib or its pharmacologically active salts in human biologically fluids. Routine therapeutic drug management of imatinib and its pharmacologically active salts by immunoassays would provide simple automated tests adapted to standard laboratory equipment. However, in order to provide such immunoassays, antibodies specific to imatinib and its pharmacologically active salts must be produced. The derivatives and immunogen used in this assay must impart through these corresponding antibodies produced specific reactivity to imatinib and its pharmacologically active salts without any substantial cross reactivity to therapeutically active or inactive or pharmacologically active or inactive metabolites of imatinib and their salts. In order to be effective in monitoring drug levels, the antibodies should be specific to imatinib and its pharmacologically active salts and not cross reactive with N-desmethyl imatinib The active metabolite of imatinib which occurs in samples of patients treated with imatinib and its salts is N-desmethyl imatinib which has the formula:

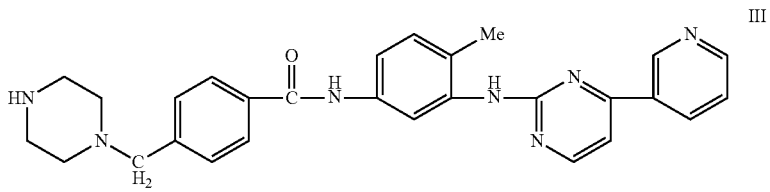

III

It is this pharmacologically active metabolite which prevents accurate determination imatinib and its salts by immunoassays of samples of patients treated with imatinib and its salts. Therefore it is long been desired to provide antibodies specific to imatinib and its pharmacologically active salts and not cross reactive with N-desmethyl imatinib

SUMMARY OF INVENTION

In accordance with this invention, a new class of antibodies have been produced which are substantially selectively reactive to imatinib and its pharmacologically active salts so as to selectively bind to imatinib and its pharmacologically active salts without any substantial cross reactivity to the its pharmacologically active imatinib metabolite, N-desmethyl imatinib. By selectively reactivity, it is meant that this antibody only reacts with the imatinib and its pharmacologically active salts and does not substantially react with the pharmacologically active imatinib metabolite, N-desmethyl imatinib The N-desmethyl imatinib metabolite prevents an accurate determination by an immunoassay of the presence and the amount of imatinib and its pharmacologically active salts in human biological fluids.

It has been found that by using immunogens which are conjugates of a carrier containing an immunogenic polymer having a reactive thiol or amino functional group with a compound of the formula:

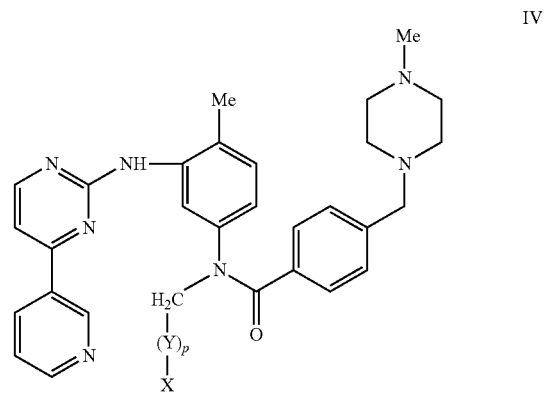

IV or its pharmacologically active salts.
  wherein Y is an organic spacing group;
  X is a terminal functional group capable of binding to said carrier through said amino or thiol group and;
  p is an integer from 0 to 1;

to produce antibodies which are specific for imatinib or its pharmacologically active salts and do not substantially react with or bind to N-desmethyl imatinib. In addition these antibodies display substantially no cross reactivity with any of its therapeutically active or inactive imatinib metabolites The provision of these antibodies which substantially selectively react with imatinib and its pharmacologically active salts and do not cross react with N-desmethyl imatinib allows one to produce an immunoassay which can specifically detect and quantify so as to monitor imatinib and its pharmacologically active salts in the fluid samples of patients being treated with imatinib or its pharmacologically active salts. Also included within this invention are reagents and kits for said immunoassay. The presence of the active metabolite of imatinib, N-desmethyl imatinib, is the major cause for inaccurate readings in immunoassays for imatinib or its pharmacologically active salts.

DETAILED DESCRIPTION

In accordance with this invention, a new class of antibodies is provided which substantially selectively reacts with imatinib or its pharmacologically active salts and do not substantially react or cross react with its metabolites as mentioned hereinabove. It has been discovered that through the use of these derivatives of imatinib of formula IV as immunogens, this new class of antibodies of this invention is provided. It is through the use of these antibodies that an immunoassay, including reagents and kits for such immunoassay for detecting and/or quantifying imatinib and its pharmacologically active salts in blood, plasma or other body fluid samples has been developed. By use of this immunoassay, the presence and amount of imatinib or its pharmacologically active salts in body fluid samples of patients being treated this chemotherapeutic agent can be detected and/or quantified. In this manner, a patient being treated with imatinib or its pharmacologically active salts can be monitored during therapy and his treatment adjusted in accordance with said monitoring. By means of this invention one achieves the therapeutic drug management of imatinib or its pharmacologically active salts in cancer patients being treated with imatinib or its pharmacologically active salts as a chemotherapeutic agent.

The chemotherapeutic agent to be detected is imatinib of formula I or its pharmacologically active salts. These salts include the acid addition salts for example salts for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxybenzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2 sulfonic acid. The preferred acid is methane sulfonic acid.

The reagents utilized in the assay of this invention are conjugates of a carrier having a reactive thiol or amino functional group with the compounds of formula IV. These conjugates are competitive binding partners with the imatinib and its pharmacologically active salts present in the sample for the binding with the antibodies of this invention. Therefore, the amount of conjugate reagent which binds to the antibody will be inversely proportional to the amount of imatinib and its pharmacologically active salts in the sample. In accordance with this invention, the assay utilizes any conventional measuring means for detecting and measuring the amount of said conjugate which is bound or unbound to the antibody. Through the use of said means, the amount of the bound or unbound conjugate can be determined. Generally, the amount of imatinib or its pharmacologically active salts in a sample is determined by correlating the measured amount of the bound or unbound conjugate produced by the imatinib or its pharmacologically active salts in the sample with values of the bound or unbound conjugate determined from standard or calibration curve obtained with samples containing known amounts of imatinib or its pharmacologically active salts, which known amounts are in the range expected for the sample to be tested. These studies for producing calibration curves are determined using the same immunoassay procedure as used for the sample.

Definitions

Throughout this description the following definitions are to be understood:

The term "Ph" as used throughout this application designates a phenyl radical. The term "alkylene" designates a divalent saturated straight or branch chain hydrocarbon substituent containing from one to ten carbon atoms The terms "immunogen" and "immunogenic" refer to substances capable of eliciting, producing, or generating an immune response in an organism.

The term "conjugate" refers to any substance formed from the joining together of separate parts. Representative conjugates in accordance with the present invention include those formed by the joining together of a small molecule, such as the compound of formula IV, and a large molecule, such as a carrier having one or more reactive thiol or amino functional group, which carrier can be a polyamine polymer, particularly protein. In the conjugate the small molecule maybe joined at one or more active sites on the large molecule. The term conjugate includes the term immunogen.

"Haptens" are partial or incomplete antigens. They are protein-free substances, mostly low molecular weight substances, which are not capable of stimulating antibody formation, but which do react with antibodies. The latter are formed by coupling a hapten to a high molecular weight immunogenic carrier and then injecting this coupled product, i.e., immunogen, into a human or animal subject. The hapten of this invention is imatinib or its pharmacologically active salts.

As used herein, a "spacing group" or "spacer" refers to a portion of a chemical structure which connects two or more substructures such as haptens, carriers, immunogens, labels, or tracers through a functional linking group. These spacer groups will be enumerated hereinafter in this application. The atoms of a spacing group and the atoms of a chain within the spacing group are themselves connected by chemical bonds. Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen and sulfur. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer.

An "immunogenic carrier," as the terms are used herein, is an immunogenic substance, commonly a protein or a protein modified to contain a reactive thiol or amino group, that can join at one or more positions with a hapten, in this case imatinib, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation.

Also various protein types may be employed as a polyamino acid) immunogenic carrier. These types include albumins, serum proteins, lipoproteins, etc. Illustrative proteins include bovine serum albumin (BSA), keyhole limpet hemocyanin (KLH), egg ovalbumin, bovine thyroglobulin (BTG) etc. Alternatively, synthetic poly(amino acids) may be utilized.

Immunogenic carriers can also include poly amino-polysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the α-amino group of each amino acid residue (except the $NH_2$ terminus) is linked to the α-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments.

The term "derivative" refers to a chemical compound or molecule made from a parent compound by one or more chemical reactions.

The term "carrier" refers to solid particles and/or polymeric polymers having a reactive thiol or amino functional group such as immunogenic polymers such as those mentioned above. Where the carrier is a solid particle, the solid particle may be bound, coated with or otherwise attached to a polyamine polymer to provide one or more reactive sites for bonding to the terminal functional group X in the compounds of the formula IV. On the other hand the immunoassay of this invention can be carried out by coating the antibody on the solid particles.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for Imatinib or its pharmacologically active salts. The kit may further comprise ligands of the analyte and calibration and control materials. The reagents may remain in liquid form or may be lyophilized.

The phrase "calibration and control materials" refers to any standard or reference material containing a known amount of a drug to be measured. The concentration of drug is calculated by comparing the results obtained for the unknown specimen with the results obtained for the standard. This is commonly done by constructing a calibration curve.

The term "biological sample" includes, but is not limited to, any quantity of a substance from a living thing or formerly living thing. Such living things include, but are not limited to, humans, mice, monkeys, rats, rabbits, horses, and other animals. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Reagents and Immunogens

In an immunoassay based upon an antibody, a conjugate of imatinib is constructed to compete with the imatinib and its pharmacologically active salts in the sample for binding sites on the antibody. In the immunoassay of this invention, the reagents of formula IV are the nitrogen substituted imatinib derivatives formed on the amide bridge of imatinib of formula I. In the compounds of formula IV, the linker spacer constitutes the "Y—X" portion of this molecule. This linker X and the spacer—"Y" are conventional in preparing conjugates for immunoassays and immunogens for producing antibodies. Any of the conventional spacer-linking groups utilized to prepare conjugates for immunoassays and immunogens for producing antibodies can be utilized in the compounds of formula IV. Such conventional linkers and spacers are disclosed in U.S. Pat. No. 5,501,987 and U.S. Pat. No. 5,101,015.

The conjugates as well as the immunogens, are prepared from the compound of the formula I. In the conjugates or immunogens of the carrier with the hapten, the carriers are linked in one or positions to one or more reactive amino or thiol groups contained by the polymeric portion of the carrier to the hapten which has the formula:

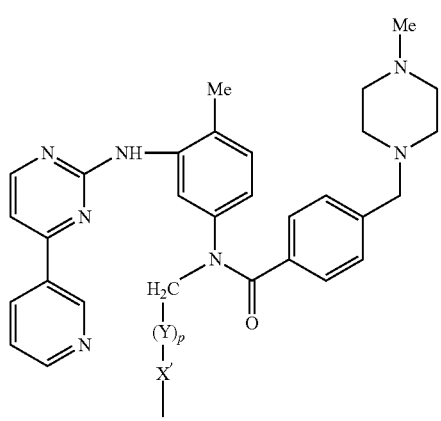

IVA wherein X' is a functional linking group capable of binding to said carrier through said amino or thiol group and p and Y are as above;

Among the preferred spacer groups are included the spacer groups hereinbefore mentioned. Particularly preferred spacing groups are groups such as alkylene containing from 1 to 10 carbon atoms,

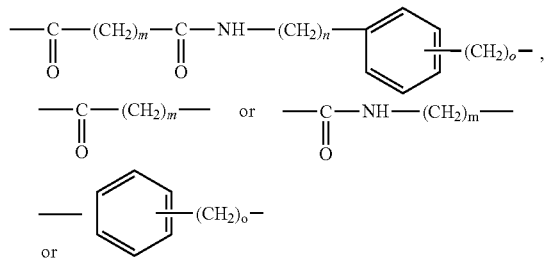

wherein n and o are integers from 0 to 6, and m is an integer from 1 to 6 with alkylene being the especially preferred spacing group.

In the compounds of formula IV-A, where X' is a functional group linking the spacer, preferably through a reactive amine or thiol group on the polymeric carrier. The group X' is the result of the terminal functional group X in the compounds of formula IV binding to the reactive amino or thiol group in the polymer of the carrier or the immunogen. Any terminal functional group capable of reacting with an amino or thiol group can be utilized as the functional group X in the compounds of formula IV. These terminal functional groups preferably included within X are:

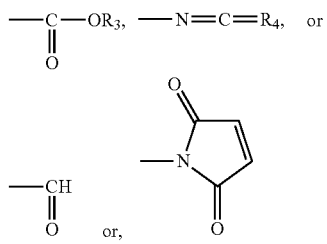

wherein $R_3$ is hydrogen or taken together with its attached oxygen atom forms a reactive ester and $R_4$ is oxygen or sulfur. The radical —N=C=$R_4$, can be an isocyanate or as isothiocyanate. The active esters formed by $OR_3$ include imidoester, such as N-hydroxysuccinamide, 1-hydroxy benzotriazole and p-nitrophenyl ester. However any active ester which can react with an amine group can be used.

When X in the compound of formula IV is

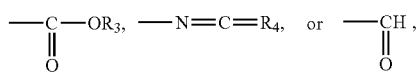

these compounds preferably react with the free amino group of the polymeric or immunogenic carrier. On the other hand, when X in the compound of formula IV is the maleimide radical of the formula

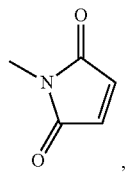

this compound preferably reacts with the thiol (or SH) group which may be present on the polymeric or protein carrier, including the immunogens, to produce the maleimide functional group as X' in the compounds of the formula IV-A.

In accordance with an embodiment, of this invention where X' is a maleimide in the compounds of formula IV is attached to a polymeric protein which has been modified to convert a reactive amino group to a thiol group. This can be done by the reacting a free amino group of a polymeric protein carrier with a compound of the formula

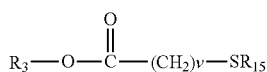

VI wherein $R_{15}$ is a thiol protecting group;
$R_3$ is as above; and
v is an integer of from 1 to 4.

In this manner, the thiol group, SH— becomes the functional group of the carrier bonded to the remainder of the carrier. The reaction to convert the reactive amino group of the protein is carried out in an aqueous medium by mixing the protein containing carrier with the compound of formula VI in an aqueous medium. In this reaction temperature and pressure are not critical and the reaction can be carried out at room temperature and atmospheric pressure. Temperatures of from 10° C. to 25° C. are generally preferred. In the next step before the thiol modified carrier is reacted with the compound of formula W after the thiol protecting group of carrier is removed by conventional means from the resulting reaction product of the compound of formula V with the protein carrier.

Any conventional means for removing a thiol protecting group can be utilized in carrying out this reaction. However, in utilizing a means to remove the thiol protecting group, care must be taken that the reactants be soluble in the aqueous medium and do not in any way destroy or harm the polyamine polymer contained in the carrier. A preferred means for removing this protecting group is by the use of dithiothreitol as an agent to reduce the resultant condensation product. This reduction can be carried out by simply adding the reducing agent to the reaction medium without utilizing higher pressures or temperatures. This reduction can be carried out at room temperature and atmospheric pressure. Any conventional thiol protecting agent can be utilized in the compound of formula VI. The thiol protecting groups are well known in the art with 2-pyridyldithio being the preferred protecting group.

While the above method represents one means for converting a reactive terminal amino group on the polyamine polymeric containing carrier to a thiol group, any conventional means for carrying out this conversion can be utilized. Methods for converting terminal amino groups on polyamine polymeric containing carriers to thiols are well known in the art and can be employed in accordance with this invention.

The reaction of the polymeric polyamine containing carrier having a terminal reactive thiol group with the compound of formula IV where X is a functional group capable of binding to the terminal thiol group carried by the carrier can be carried out by conventional means. In the preferred embodiment the maleimide of carried by X in the compound formula IV is reacted with the thiol group carried by the polyamine polymeric carrier. Any well known means for addition of a thiol across a maleimide double bond can be utilized in producing the conjugates of formula VI A which are conjugated through a thiol bridge.

The carboxylic group and the active esters are coupled to the carrier or immunogenic polymer by conventional means. The amine group on the polyamine polymer, such as a protein, produces an amide group which connects the spacer to the polymer, immunogens or carrier and/or conjugates of this invention.

In the immunogens and conjugates of the present invention, the chemical bonds between the carboxyl group-containing imatinib hapten and the reactive amino groups on the polyamine polymer contained by the carrier or immunogen can be established using a variety of methods known to one skilled in the art. It is frequently preferable to form amide bonds. Amide bonds are formed by first activating the carboxylic acid moiety in the compounds of formula IV-A by reacting the carboxy group with a leaving group reagent (e.g., N-hydroxysuccinimide, 1-hydroxybenzotriazole, p-nitrophenol and the like). An activating reagent such as dicyclohexylcarbodiimide, diisopropylcarbodiimide and the like can be used. The activated form of the carboxyl group in the imatinib hapten of formula VI-A is then reacted with a buffered solution containing the carrier with the reactive amino group.

On the other hand where X is a terminal isocyanate or thioisocyanate radical in the compound of formula IV, these radicals when reacted with the free amine of a polyamine polymer produce the conjugate or immunogen of formula IV-A where X' is

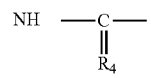

with the amino group on the polyamine carrier or the immunogenic polypeptide.

Where X, in the compounds of formula IV contains an aldehyde radical, these compounds may be connected to the free amino group of the polyamine polypeptide on the carrier through an amine linkage by reductive amination. Any conventional method of condensing an aldehyde with an amine such as through reductive amination can be used to form this linkage. In this case, X' in the ligand portions of formula IV is —$CH_2$—.

The compounds of formula IV are formed by reacting imatinib of formula I with a halide of the formula:

halo-$CH_2$—$(Y)_p$—X            VII wherein p, Y and X are as above
to form the compound of formula IV. Any conventional means of reacting a halide with the nitrogen on the amide can be utilized in condensing the compound of formula VII to this amide position on the imatinib of formula I. The use of a halide in the compound of formula VII provides an efficient means for forming such a substituted amide by condensing with the amide group on the compound of formula I.

Where the compound of formula I is in the form of its salt it is necessary to convert this salt to its free base before reacting with the compound of formula V to form the compound of formula IV. This can be carried out by conventional means such as neutralization of the salt. Where the salt is a basic salt, neutralization can be accomplished in an aqueous media by addition of an acid. Where the salt is an acid addition salt neutralization is accomplished in an aqueous media by addition of a base.

The compound of formula IV can be converted into the immunogens and/or the conjugate reagents of this invention by reacting these compounds with a carrier containing a polyamine or a polypeptide. The same polypeptide can be utilized as the carrier and as the immunogenic polymer in the immunogen of this invention provided that polyamine or polypeptide is immunologically active. However, to form the conjugates, these polymers need not produce an immunological response as needed for the immunogens. In accordance with this invention, the various functional group represented by X in the compounds of formula IV can be conjugated to the carrier containing polymer with a reactive amino group by conventional means of attaching a functional group to an amino group contained within the polymer. In accordance with a preferred embodiment, in the compound of formula IV where the attachment is through a reactive amino group on the carrier, X is a carboxylic acid group or an active ester thereof.

Antibodies

The present invention also relates to novel antibodies including monoclonal antibodies to imatinib or its pharmacologically active salts produced by utilizing the aforementioned immunogens. In accordance with this invention it has been found that these antibodies produced in accordance with this invention are selectively reactive with imatinib or its pharmacologically active salts and do not react with N-desmethyl imatinib which interferes with immunoassays for imatinib and its pharmacologically active salts. The ability of the antibodies of this invention not to react with N desmethyl imatinib makes these antibodies provide an immunoassay for detecting the presence and/or quantifying the amount of imatinib and its pharmacologically active salts in patient fluid samples The present invention relates to novel antibodies and monoclonal antibodies to imatinib or its pharmacologically active salts. The antisera of the invention can be conveniently produced by immunizing host animals with the immunogens of this invention. Suitable host animals include rodents, such as, for example, mice, rats, rabbits, guinea pigs and the like, or higher mammals such as goats, sheep, horses and the like. Initial doses, bleedings and booster shots can be given according to accepted protocols for eliciting immune responses in animals, e.g., in a preferred embodiment mice received an initial dose of 100 ug immunogen/mouse, i.p. and two or more subsequent booster shots of between 50 and 100 ug immunogen/mouse over a six month period. Through periodic bleeding, the blood samples of the immunized mice were observed to develop an immune response against imatinib or its pharmacologically active salts binding utilizing conventional immunoassays. These methods provide a convenient way to screen for hosts which are producing antisera having the desired activity. The antibodies were also screened against the major metabolites of imatinib or its pharmacologically active salts and showed no substantial binding to these compounds.

Monoclonal antibodies are produced conveniently by immunizing Balb/c mice according to the above schedule followed by injecting the mice with 100 ug immunogen i.p. or i.v. on three successive days starting four days prior to the cell fusion. Other protocols well known in the antibody art may of course be utilized as well. The complete immunization protocol detailed herein provided an optimum protocol for serum antibody response for the antibody to imatinib or its pharmacologically active salts.

B lymphocytes obtained from the spleen, peripheral blood, lymph nodes or other tissue of the host may be used as the monoclonal antibody producing cell. Most preferred are B lymphocytes obtained from the spleen. Hybridomas capable of generating the desired monoclonal antibodies of the invention are obtained by fusing such B lymphocytes with an immortal cell line, which is a cell line that which imparts long term tissue culture stability on the hybrid cell. In the preferred embodiment of the invention the immortal cell may be a lymphoblastoid cell or a plasmacytoma cell such as a myeloma cell, itself an antibody producing cell but also malignant. Murine hybridomas which produce Imatinib or its pharmacologically active salts monoclonal antibodies are formed by the fusion of mouse myeloma cells and spleen cells from mice immunized against Imatinib or its pharmacologically active salts-protein conjugates. Chimeric and humanized monoclonal antibodies can be produced by cloning the antibody expressing genes from the hybridoma cells and employing recombinant DNA methods now well known in the art to either join the subsequence of the mouse variable region to human constant regions or to combine human framework regions with complementary determining regions (CDR's) from a donor mouse or rat immunoglobulin. An improved method for carrying out humanization of murine monoclonal antibodies which provides antibodies of enhanced affinities is set forth in International Patent Application WO92/11018.

Polypeptide fragments comprising only a portion of the primary antibody structure may be produced, which fragments possess one or more immunoglobulin activities. These polypeptide fragments may be produced by proteolytic cleavage of intact antibodies by methods well known in the art, or by inserting stop codons at the desired locations in expression vectors containing the antibody genes using site-directed mutagenesis to produce Fab fragments or (Fab')$_2$ fragments. Single chain antibodies may be produced by joining VL and VH regions with a DNA linker (see Huston et al., *Proc. Natl. Acad. Sci. U.S.A.*, 85:5879-5883 (1988) and Bird et al., *Science*, 242:423-426 (1988))

The antibodies of this invention are selective for imatinib and its pharmacologically active salts without having any substantial cross-reactivity with N-des methyl imatinib. In addition these antibodies display substantially no cross reactivity with any of its therapeutically active or inactive imatinib metabolites. By having no substantial cross-reactivity it is meant that the antibodies of this invention have a cross reactivity relative to imatinib and its pharmacologically active salts with these metabolites, particularly N-des methyl imatinib, of less than 15%, preferably less than 10%.

Immunoassays

In accordance with this invention, the conjugates and the antibodies generated from the immunogens of these compounds of formula IV can be utilized as reagents for the determination of imatinib or its pharmacologically active salts in patient samples. This determination is performed by means of an immunoassay. Any immunoassay in which the reagent conjugates formed from the compounds of formula IV compete with the imatinib or its pharmacologically active salts in the sample for binding sites on the antibodies generated in accordance with this invention can be utilized to determine the presence of imatinib or its pharmacologically active salts in a patient sample. The manner for conducting such an assay for imatinib or its pharmacologically active salts in a sample suspected of containing imatinib or its pharmacologically active salts, comprises combining an (a) aqueous medium sample, (b) an antibody to imatinib or its pharmacologically active salts generated in accordance with this invention and (c) the conjugates formed from the compounds of formula IV or mixtures thereof. The amount of imatinib or its pharmacologically active salts in the sample can be determined by measuring the inhibition of the binding to the specific antibody of a known amount of the conjugate added to the mixture of the sample and antibody. The result of the inhibition of such binding of the known amount of conjugates by the unknown sample is compared to the results obtained in the same assay by utilizing known standard solutions of imatinib or its pharmacologically active salts. In determining the amount of imatinib or its pharmacologically active salts in an unknown sample, the sample, the conjugates formed from the compounds of formula IV and the antibody may be added in any order.

Various means can be utilized to measure the amount of conjugate formed from the compounds of formula IV bound to the antibody. One method is where binding of the conjugates to the antibody causes a decrease in the rate of rotation of a fluorophore conjugate. The amount of decrease in the rate of rotation of a fluorophore conjugate in the liquid mixture can be detected by the fluorescent polarization technique such as disclosed in U.S. Pat. No. 4,269,511 and U.S. Pat. No. 4,420,568.

On the other hand, the antibody can be coated or absorbed on nanoparticles so that when these particles react with the imatinib or its pharmacologically active salts conjugates formed from the compounds of formula IV, these nanoparticles form an aggregate. However, when the antibody coated or absorbed nanoparticles react with the imatinib or its pharmacologically active salts in the sample, the imatinib or its pharmacologically active salts from the sample bound to these nanoparticles does not cause aggregation of the antibody nanoparticles. The amount of aggregation or agglutination can be measured in the assay mixture by absorbance.

On the other hand, these assays can be carried out by having either the antibody or the imatinib or its pharmacologically active salts conjugates attached to a solid support such as a microtiter plate or any other conventional solid support including solid particles. Attaching antibodies and proteins to such solid particles is well known in the art. Any conventional method can be utilized for carrying out such attachments. In many cases, in order to aid measurement, labels may be placed upon the antibodies, conjugates or solid particles, such as radioactive labels or enzyme labels, as aids in detecting the amount of the conjugates formed from the compounds of formula IV which is bound or unbound with the antibody. Other suitable labels include chromophores, fluorophores, etc.

As a matter of convenience, assay components of the present invention can be provided in a kit, a packaged combination with predetermined amounts of new reagents employed in assaying for imatinib or its pharmacologically active salts. These reagents include the antibody of this invention, as well as, the conjugates formed from the compounds of formula IV.

In addition to these necessary reagents, additives such as ancillary reagents may be included, for example, stabilizers, buffers and the like. The relative amounts of the various reagents may vary widely to provide for concentrations in solution of the reagents which substantially optimize the sensitivity of the assay. Reagents can be provided in solution or as a dry powder, usually lyophilized, including excipients which on dissolution will provide for a reagent solution having the appropriate concentrations for performing the assay.

EXAMPLES

In the examples, the following abbreviations are used for designating the following:

| | |
|---|---|
| NaH | sodium hydride |
| THF | tetrahydrofuran |
| DMF | dimethylformamide |
| LiOH | lithium hydroxide |
| EDC | 1-(3-dimethylaminopropyl)-3-ethylcarbodiimide hydrochloride |
| Sulfo-NHS | N-hydroxysulfosuccinimide |
| DMSO | dimethylsulfoxide |
| MeOH | methanol |
| $CH_2Cl_2$ | dichloromethane |
| APCI | atmospheric pressure chemical ionizatin mass spectrometry |
| TLC | thin layer chromatography |
| HOAc | acetic acid |
| $CHCl_3$ | chloroform |
| HPLC | high pressure liquid chromatography |
| ANS | 8-Anilino-1-naphthalenesulfonic acid |
| HRP | horse radish-peroxidase |
| TMB | 3,3',5,5'-Tetramethylbenzidine |
| TRIS | Tris(hydroxymethyl)aminomethane hydrochloride |
| BSA | bovine serum albumin |
| KLH | Keyhole Limpet Hemocyanin |
| PBS | phosphate buffered saline |
| $diH_2O$ | deionized water |

In the examples, Scheme 1 below set forth the specific compounds prepared and referred to by numbers in the Examples. The phosphate buffer composition has an aqueous solution containing 15.4 mM Sodium phosphate dibasic ($Na_2HPO_4$)

4.6 mM Sodium phosphate monobasic ($NaH_2PO_4$)

pH=7.2±0.10

The ether used in the Examples was diethyl ether. Parts or percentages given in these examples are parts by volume.

Scheme 1

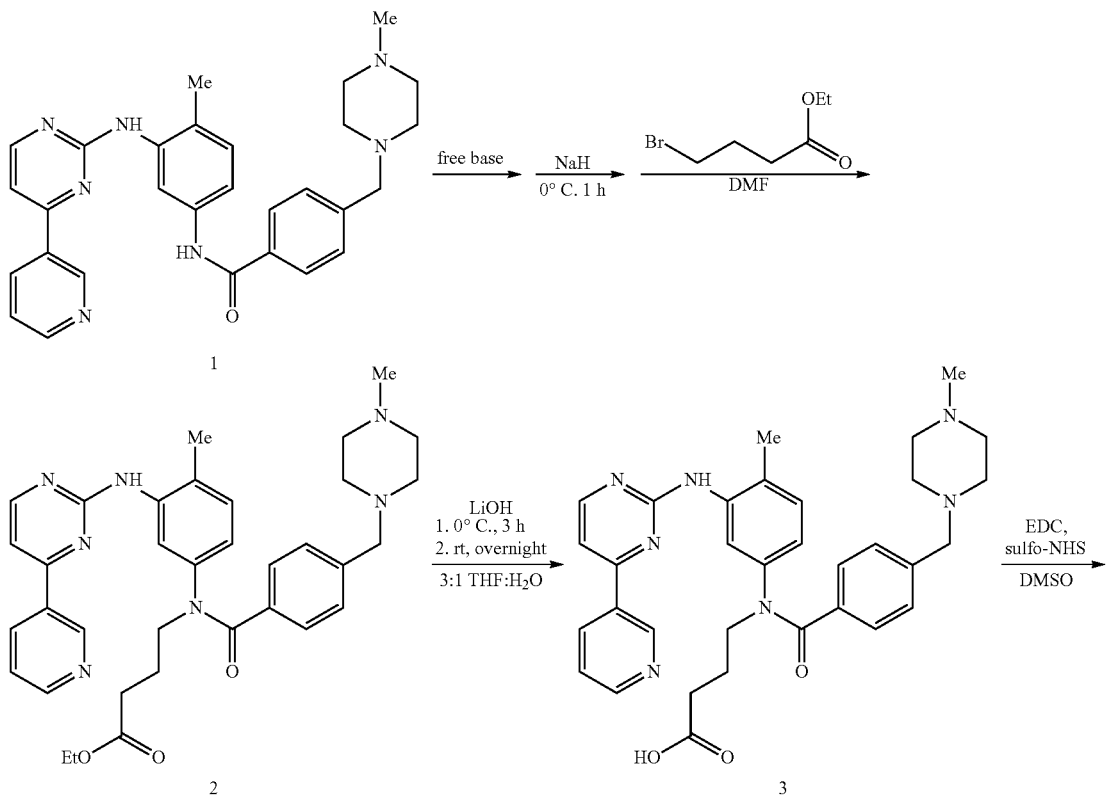

-continued

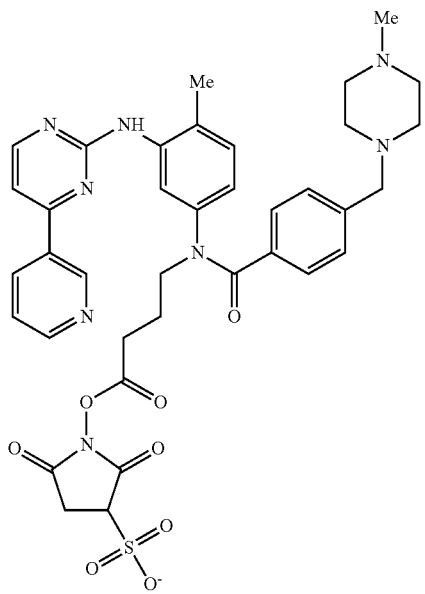

4

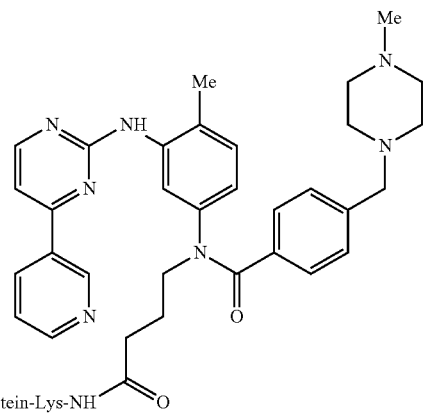

5

EXAMPLES

Example 1

Extraction of Imatinib Mesylate

Fourteen tablets, each containing 400 mg of the imatinib as the mesylate salt, were crushed to a fine powder with a mortar and pestle; the tablet coating was not first removed. The powder of the crushed tablets was stirred in 1500 mL 10% MeOH (by volume)/$CH_2Cl_2$ for four hours. The mixture from the crushed tablets containing imatinib mesylate was filtered through Celite and the solvent stripped off to yield 7.14 g of a yellow solid containing imatinib mesylate. The yellow solid containing imatinibin mesylate was dissolved in 75 mL of warm 20% chloroform (by volume) in ethanol to produce a solution of imatinib mesylate, then 50 mL of 1:1 ether:ethanol (volume:volume) was added, causing the solution of imatinib mesylate to become cloudy. Cooling in ice induced precipitation of the imatinib mesylate, which continued to progress with the slow addition of ether. The precipitated imatinib mesylate was layered with ether, covered, and allowed to stand overnight.

The precipitated imatinib mesylate was collected by filtration and washed with 50 mL cold 10% (by volume) ethanol in ether, then dried under vacuum to yield 6.42 g (115%) of imatinib mesylate as a light yellow solid. Recrystallization of imatinib mesylate from chloroform/ethanol with the aid of ether was carried out a second time to yield 4.45 g (79%) of imatinib mesylate as a light yellow solid. This light yellow solid of imatinib mesylate isolated from the tablets was used in Example 2. The structure was confirmed by NMR and elemental analysis. The purity was confirmed by HPLC.

Example 2

Preparation of Imatinib Free Base

The imatinib mesylate salt (1) (1.01 g, 1.71 mmol) prepared in Example 1 was added to 250 mL of dichloromethane to form a suspension of imatinib mesylate. 50 mL of 10% saturated aqueous $NaHCO_3$ was added and mixed well with the suspension of imatinib mesylate in dichloromethane to produce the free base of imatinib in the organic layer (dichloromethane). The emulsion formed from the aqueous $NaHCO_3$ and the dichloromethane was removed by filtration, producing an organic layer of dichloromethane containing the imatinib as the free base and an aqueous layer. The organic layer of dicholomethane containing imatnnb as the free base was separated from the aquesou layer. The organic layer was dried over $Na_2SO_4/MgSO_4$. To isolate the imatinib free base, the organic layer (dichloromethane) was filtered to remove the $Na_2SO_4/MgSO_4$ and then stripped off, producing a solid containing the free base of imatinib. Toluene was added to the solid containing imatinib free base and flash evaporated three times and then dried under vacuum to remove any residual water. The free base of imatinib was obtained as a white solid and used in example 3. The free base of imatinib exhibited $^1H$, $^{13}C$ NMR and APCI data consistent with the structure. NMR assignments were based on a DQF-COSY experiment.

Example 3

Preparation of Butyric Acid Ethyl Ester of Imatinib

The dried free base of imatinib prepared in example 2 was dissolved in 35 mL dry DMF under nitrogen and cooled in ice. The mixture containing imatinib was stirred effectively and solid sodium hydride (60% dispersion in mineral oil, 0.111 g, 2.78 mmol, 1.6 eq) was added all at once. A solution of ethyl 4-bromobutyrate (0.59 g, 3.0 mmol, 1.8 eq) in 3.5 mL DMF was slowly added via syringe to the mixture containing imatinib, and the reaction to produce the butyric acid ethyl ester of imatinib (2) was allowed to proceed overnight, warming to ambient temperature with the bath. In situ analysis of the reaction mixture by APCI(+) showed m/z=608.3 (100%), 494.2 (30%), and 722.4 (5%) amu, corresponding to the butyric acid ethyl ester of imatinib (2), imatinib starting material, and a di-butyric acid ethyl ester of imatinib, respectively.

The reaction mixture was diluted with 100 mL dichloromethane, cooled in ice and quenched with 10 mL water. The dichloromethane containing the butyric acid ethyl esters of imatinib and aqueous layers were separated. To increase the yield the aqueous layer was extracted with 3×50 mL dichloromethane and 2×25 mL ethyl acetate. The combined organic fractions containing the butyric acid ethyl ester derivates of imatinib were stripped leaving a mixture of imatinib derivatives. To isolate the butyric acid ethyl ester of imatinib, the mixture was chromatographed on 100 g silica gel using a 5-50% methanol/dichloromethane gradient. The resulting butyric acid ethyl ester of imatinib (2) had mass 0.61 g (59%) TLC $R_f$=0.36 (1:4:0.05 MeOH: CHCl$_3$: HOAc). APCI (+) m/z=608.3 amu.

Example 4

Hydrolysis of Imatinib Butyric Acid Ethyl Ester

4-{[4-(4-methyl-piperazin-1-ylmethyl)-benzoyl]-[4-methyl-3-(4-pyridin-3-yl-pyrimidin-2-ylamino)-phenyl]-amino}-butyric acid ethyl ester (2) (1.21 g, 2.0 mmol, 1 eq) was dissolved in 60 mL THF and cooled in ice. A solution of LiOH.H$_2$O (0.28 g, 6.7 mmol, 3.4 eq) in 20 mL water was added dropwise while stirring. This hydrolysis reaction was incubated for 3 h at 0° C. and then allowed to proceed overnight, while warming to room temperature to produce the free acid, imatinb butyric acid.

After cooling the reaction mixture containing the imatinb butyric acid in ice, 0.5 M HCl (aq) was added dropwise to obtain a pH 5-6. The volatile solvents were stripped to afford a crude reaction product containing the imatinib butyric acid as a white solid. To remove impurities the crude reaction product was triturated in water, collected by filtration, and dried under vacuum and then triturated in ether to provide the butyric acid derivative of imatinib, compound 3, as a yellow solid, mass 0.99 g (86%) as the partial HCl salt. Melting point: 203-207° C. (dec). TLC $R_f$=0.26 (7:1:0.1) CH$_2$Cl$_2$: MeOH: NH$_4$OH. APCI (+) m/z=580.2 amu. $^1$H NMR (dmso-d$_6$, 80° C.) is consistent with the structure. Analysis for C$_{33}$H$_{37}$N$_7$O$_3$.1.65H$_2$O.0.1HCl requires C, 64.48; H, 6.25; N, 15.83; Cl, 0.63. Found C, 64.65; H, 6.64; N, 15.99; Cl, 0.58. HPLC purity was 100%.

Example 5

Preparation of Sulfo-NHS Activated Ester of Imatinib

Imatinib butyric acid (3) was derivatized by reaction with EDC and sulfo-NHS to produce the sulfo-NHS activated ester of imatinib for eventual conjugation to the proteins (examples 6a, b, 7). To a stirred 5 mL of anhydrous DMSO compound 3 (94 mg, 0.16 mmol) was added, followed by EDC (94 mg, 0.49 mmol) and sulfo-NHS (107 mg, 0.49 mmol). The reaction mixture was stirred at room temperature for 18 hours under nitrogen to produce the sulfo-NHS activated ester of imatinib. The reaction mixture was used directly in Examples 6a and 6b.

Example 6a

Preparation of Imatinib Immunogen

A protein solution of KLH was prepared by dissolving 300 mg of KLH in 19.6 mL of phosphate buffer (50 mM, pH 7.5) and then slowly adding 39.2 mL of DMSO while stirring the protein solution of KLH on ice. Stirring was continued for an additional 30 minutes at room temperature, followed by addition of sulfo-NHS activated imatinib derivative (4) prepared in Example 5 (2.532 mL, 0.08 mmol). The reaction mixture of KLH and activated imatinib derivative (4) was allowed to stir for 18 hours at room temperature in an amber glass bottle producing an imatinib-KLH conjugate (5). The imatinib-KLH conjugate was then purified by dialysis against 66% DMSO in phosphate buffer (50 mM, pH 7.5) at room temperature. Thereafter the DMSO proportion was reduced stepwise: 60%, 50%, 40%, 20%, 10% and 0%. The last dialysis was performed against phosphate buffer at 4° C. The imatinib-KLH conjugate (5) was characterized by ultraviolet-visible spectroscopy. The conjugate was diluted to a final concentration of 2 mg/mL in phosphate buffer (50 mM, pH 7.5).

Example 6b

Preparation of Imatinib Immunogen

Imatinib immunogen was prepared as in Example 6a except the imatinib-KLH conjugate (5) was diluted to a final concentration of 2 mg/mL in phosphate buffer and DMSO (50% by volume).

Example 7

Preparation of Imatinib-BSA Conjugate with Derivative 4

A protein solution of BSA was prepared by dissolving 1,000 mg BSA in phosphate buffer (50 mM, pH 7.5) for a final concentration of 50 mg/mL. 40 mL of DMSO was slowly added to the protein solution of BSA while stirring on ice. Stirring was continued for an additional 30 minutes at room temperature, followed by addition of sulfo-NHS activated imatinib derivative (4) prepared in Example 5 (0.437 mL, 0.014 mmol). The amount of sulfa-NHS activated imatinib derivative (4) added to the protein solution of BSA was calculated for a 1:1 molar ratio between the derivative of imatinib (4) and BSA. The mixture of BSA and activated imatinib derivative (4) was allowed to stir for 18 hours at room temperature in an amber glass bottle to produce the conjugate of the activated imatinib ester (4) and BSA. This conjugate was then purified by dialysis against 66% DMSO in phosphate buffer (50 mM, pH 7.5) at room temperature. Thereafter the DMSO to proportion was reduced stepwise: 60%, 50%, 40%, 20%, 10% and 0%. The last dialysis was performed against phosphate buffer at 4° C. The purified imatinib-BSA conjugate was characterized by UV/VIS spectroscopy.

Example 8a

Preparation of Polyclonal Antibodies to Imatinib

Two groups of ten female BALB/c mice were immunized i.p. one group with 100 μg/mouse of imatinib-KLH immunogen as prepared in Example 6a (10 mice) and the other group with 100 μg/mouse of imatinib-KLH immunogen (to mice) emulsified in Complete Freund's adjuvant as prepared Example 6b. The mice were boosted once four weeks after the initial injection with 100 μg/mouse of the same immunogens emulsified in Incomplete Freund's Adjuvant. Twenty days after the boost test bleeds containing polyclonal antibodies from each mouse were obtained by orbital bleed. The antiserum from these test bleeds contained imatinib antibodies were evaluated in Examples 9, boa and 11.

Example 8b

Preparation of Monoclonal Antibodies to Imatinib

Mice from example 8a that were immunized with imatinib-KLH prepared in 6b were used to produce monoclonal antibodies. For monoclonal antibodies starting three days before the fusion, the mice were injected i.p. with 400 μg (3 days before fusion), 200 μg (2 days before fusion), and 200 μg (1 day before fusion) of imatinib-KLH in PSS/DMSO prepared in example 6b. Spleen cells were isolated from the selected mice and fused with 2×10⁷ SP2/0 cells with 50% polyethylene glycol 1500 according to the method of Coligan, J. E. et al., eds., *Current Protocols in Immunology,* 2.5.1-2.5.8, (1992), Wiley & Sons, NY. The fused cells were plated on ten 96-well plates in DMEM/F12 supplemented with 20% Fetal-Clone I, 2% L-glutamine (100 mM) and 2% 50× HAT. Two to three weeks later, the hybridoma supernatant was assayed for the presence of anti-imatinib antibodies by ELISA (as in example fob). Cells from the wells that gave positive ELISA results (example lob) were expanded to 24 well plates. Clones positive by ELISA were subcloned twice by limiting dilution according to the method disclosed in Coligan, J. E. et al., eds., *Current Protocols in Immunology,* 2.5.8-2.5.17, (1992), Wiley & Sons, NY. Hybridoma culture supernatants containing monoclonal antibody from selected subclones were confirmed for imatinib binding by a competitive ELISA (example 11). These monoclonal antibodies were tested for imatinib binding and cross-reactivity to a major imatinib metabolite, N-desmethyl imatinib, by indirect competitive microtiter plate assay as described in example 11.

Example 9

Microtiter Plate Sensitization Procedure with Imatinib-BSA Conjugate

The ELISA method for measuring imatinib concentrations was performed in polystyrene microtiter plates (Nunc MaxiSorp F8 Immunomodules) optimized for protein binding and containing 96 wells per plate. Each well was coated with imatinib-BSA conjugate (prepared as in Example 7) by adding 300 µL of imatinib-BSA conjugate at 10 µg/mL in 0.05M sodium carbonate, pH9.6, and incubating for three hours at room temperature. The wells were washed with 0.05M sodium carbonate, pH9.6 and then were blocked with 375 µL of 5% sucrose, 0.2% sodium caseinate solution for 30 minutes at room temperature. After removal of the post-coat solution the plates were dried at 37° C. overnight.

Example 10a

Antibody Screening Procedure—Titer

This procedure is to find the dilution of antibody to be tested for displacement as in Example 11. The ELISA method for screening imatinib antibodies (produced in Example 8a and 8b) was performed with the microtiter plates that were sensitized with imatinib-BSA conjugate prepared in Example 9. The antibody screening assay was performed by diluting the murine serum from test bleeds (as in Example 8a) containing polyclonal imatinib antibodies to 1:2,000, 1:6,000, 1:20,000 and 1:50,000 (volume/volume) in phosphate buffered saline containing 0.1% BSA and 0.01% thimerosal. For evaluation of monoclonal antibodies, hybridoma supernatants of Example 8b, which were found to be positive for the presence of antibody by the procedure of Example 10b were diluted 1:2, 1:4, 1:16, etc. (volume/volume) in phosphate buffered saline containing 0.1% BSA and 0.01% thimerosal. To each well of imatinib-BSA sensitized wells (prepared in example 9)50 µL phosphate buffered saline containing 0.1% BSA and 0.01% thimerosal and 50 µL of diluted antibody were added and incubated for 10 minutes at room temperature with shaking. During this incubation antibody binds to the imatinib-conjugate passively absorbed in the wells (Example 9). The wells of the plates were washed three times with 0.02 M TRIS, 0.9% NaCl, 0.5% Tween-80 and 0.001% thimerosal, pH 7.8 to remove any unbound antibody. To detect the amount of imatinib antibody bound to the imatinib-BSA conjugate in the wells, 100 µL of a goat anti-mouse antibody—HRP enzyme conjugate (Jackson Immunoresearch) diluted to a specific activity (approximately ⅓₀₀₀) in PBS with 0.1% BSA, 0.05% ANS, 0.01% thimerosal, capable of binding specifically with murine immunoglobulins and producing a colored product when incubated with a substrate, in this example TMB were added to each well. After an incubation of 10 minutes at room temperature with shaking, during which the goat anti-mouse antibody—HRP enzyme conjugate binds to imatinib antibodies in the wells, the plates were again washed three times to remove unbound goat anti-mouse antibody—HRP enzyme conjugate. To develop a measurable color in the wells washing was followed by the addition of 100 µL of TMB (TMB Substrate, BioFx), the substrate for HRP, to develop color during a 10 minute incubation with shaking at room temperature. Following the incubation for color development, 50 µL of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and was expressed as the dilution (titer) resulting in an absorbance of 1.5. Titers were determined by graphing antibody dilution of the antibody measured x-axis) vs. absorbance 650 nm (y-axis) and interpolating the titer at an absorbance of 1.5. The titer which produced absorbance of 1.5 determined the concentration (dilution) of antibody used in the indirect competitive microtiter plate assay described in Example 11.

Example 10b

Antibody Screening Procedure—Monoclonal Screening

The ELISA method for screening imatinib monoclonal antibodies (produced in example 8b) was performed with the microtiter plates that were sensitized with imatinib-BSA as described in example 9. To each well of imatinib-BSA sensitized wells (prepared in example 9)50 µL phosphate buffered saline containing 0.1% BSA and 0.01% thimerosal and then 50 µL of monoclonal culture supernatant were added and incubated for 10 minutes at room temperature with shaking. During this incubation antibody binds to the imatinib-conjugate in the well. The wells of the plates were washed three times with 0.02 M TRIS, 0.9% NaCl, 0.5% Tween-80 and 0.001% thimerosal, pH 7.8 to remove any unbound antibody. To detect the amount of imatinib antibody bound to the imatinib-BSA conjugate in the wells, 100 µL of a goat anti-mouse antibody—HRP enzyme conjugate (Jackson Immunoresearch) diluted ⅓₀₀₀ in PBS with 0.1% BSA, 0.05% ANS, 0.01% thimerosal, capable of binding specifically with murine immunoglobulins and producing a colored product when incubated with a substrate, in this example TMB, were added to each well. After an incubation of 10 minutes at room temperature with shaking, during which the goat anti-mouse antibody—HRP enzyme conjugate binds to imatinib antibodies in the wells, the plates were again washed three times to remove unbound goat anti-mouse antibody—HRP enzyme conjugate. To develop a measurable color in the wells washing was followed by the addition of 100 µL of TMB (TMB Substrate, BioFx), the substrate for HRP, to develop color during a 10 minute incubation with shaking at room temperature. Following the incubation for color development, 50 of stop solution (1.5% sodium fluoride in di $H_2O$) was added to each well to stop the color development and after 10 seconds of shaking the absorbance was determined at 650 nm (Molecular Devices Plate Reader). The amount of antibody in a well was proportional to the absorbance measured. Samples with an absorbance of greater than three or more times background were designated as positive. Fifty samples with highest absorbance were expanded to 24 well plates, as described in Example 8b.

Example 11

Indirect Competitive Microtiter Plate Immunoassay Procedure Determining $IC_{50}$ and Cross-Reactivity for Antibodies to Imatinib The ELISA method for determining $IC_{50}$ values and cross-reactivity was performed with the microtiter plates that were sensitized with imatinib-BSA described in Examples 9. Analytes—imatinib and N-desmethyl imatinib were diluted in $diH_2O$ over a concentration range of 10 to 1,000,000 ng/mL. Each of the assays were performed by incubating 50 μL of the imatinib solution with 50 μL of one of the antibodies selected from the polyclonal antibodies produced in Example 8a with the immunogen of Example 6a and those produced in Example 8a with the immunogen of Example 6b and the monoclonal antibody produced in Example 8b. The assays were all performed by diluting the concentration of the antibodies in each of the wells to the titer determined in Example 10a. During the 10 minute incubation (R.T., with shaking) there is a competition of antibody binding for the imatinib-BSA conjugate in the well (produced in example 9) and the analyte in solution. Following this incubation the wells of the plate were washed three times with 0.02 M TRIS, 0.9% NaCl, 0.5% Tween-80 and 0.001% thimerosal, pH 7.8 to remove any material that was not bound. To detect the amount of imatinib antibody bound to the imatinib-BSA conjugate in the wells (produced in example 9), 100 μL of a goat anti-mouse antibody—HRP enzyme conjugate (Jackson Immunoresearch) diluted to a predetermined specific activity (approximately 1/3000) in PBS with 0.1% BSA, 0.05% ANS, 0.01% thimerosal, capable of binding specifically with murine immunoglobulins and producing a colored product when incubated with a substrate, in this example TMB, were added to each well. After an incubation of to minutes at room temperature with shaking, during which the goat anti-mouse antibody—HRP enzyme conjugate binds to imatinib antibodies in the wells, the plates were again washed three times to remove unbound secondary conjugate. To develop a measurable to color in the wells washing was followed by the addition of 100 μL of TMB (TMB Substrate, BioFx), the substrate for HRP, to develop color in a to minute incubation with shaking at room temperature. Following the incubation for color development, 50 of stop solution (1.5% sodium fluoride in di $H_2O$) was added to each well to stop the color development and after 20 seconds of shaking the absorbance was determined at 650 nm (Molecular Devices Plate Reader). The amount of antibody in a well was proportional to the absorbance measured and inversely proportional to the amount of imatinib in the sample. The $IC_{50}$'s of imatinib and N-desmethyl imatinib were determined by constructing dose-response curves with the absorbance in the wells plotted versus analyte concentration in the wells. The absorbance of the color in the wells containing analyte was compared to that with no analyte and a standard curve was generated. The $IC_{50}$ value for a given analyte was defined as the concentration of analyte that was required to have 50% of the absorbance of the wells containing no analyte. The cross-reactivity was calculated as the ratio of the $IC_{50}$ for imatinib mesylate to the $IC_{50}$ for N-desmethyl imatinib and expressed as a percent. When measured with this pool of antibodies, the percent cross-reactivities relative to imatinib for N-desmethyl imatinib were less than or equal to 7%. Results for polyclonal antibodies to imatinib are in table I below. When measured with selected monoclonal antibodies the percent cross-reactivities relative to imatinib for N-desmethyl imatinib were less than 4%. Results for monoclonal antibodies to imatinib are in table II.

TABLE I

Cross-reactivity of competitive immunoassay using polyclonal antibodies to imatinib (Example 8a).

| Bleed # | | 1 | 2 | 3 | 4 | 5 |
|---|---|---|---|---|---|---|
| Produced from one of two groups often mice with immunogen prepared in example: | | 6b | 6b | 6b | 6a | 6a |
| Analyte | Imatinib | 100% | 100% | 100% | 100% | 100% |
| | N-desmethyl imatinib | 1% | 5% | 2% | 7% | 1% |

TABLE II

Cross-reactivity of competitive immunoassay using monoclonal antibodies to imatinib (Example 8b).

| | Monoclonal antibody number | |
|---|---|---|
| Analyte | 9F2-4-29 | 9F2-4-31 |
| Imatinib | 100% | 100% |
| N-desmethyl imatinib | 2.7% | 3.2% |

As seen from Tables I and II, the antibodies produced in accordance with this invention which were substantially reactive with imatinib mesylate and substantially non-reactive with the metabolite, N-desmethyl imatinib.

What is claimed:

1. An antibody which binds selectively to imatinib and its pharmacologically active salts without having any substantial cross-reactivity with N-desmethyl imatinib.

2. The antibody of claim 1, wherein said antibody is derived from mice, rabbits or rats.

3. The antibody of claim 1, wherein said antibody is a polyclonal antibody.

4. The antibody of claim 3, wherein said antibody is a monoclonal antibody.

5. The antibody of claim 1, wherein said antibody is derived from an immunogen of an immunogenic carrier containing a polymer having either a reactive thiol or amino group conjugated with a compound of the formula:

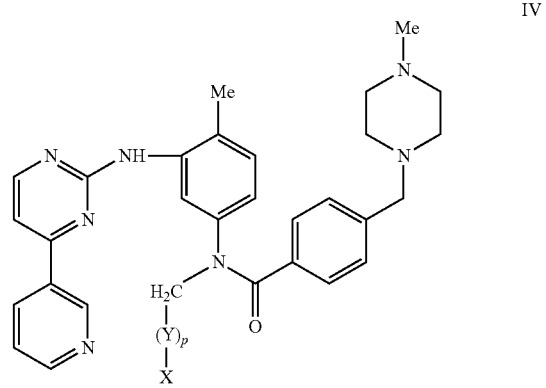

IV or its pharmacologically active salts;
wherein Y is an organic spacing group;
X is a terminal functional group capable of binding to said carrier through said amino or thiol group and;
p is an integer from 0 to 1.

6. A kit for determining the presence of imatinib or its pharmacologically active salts in a patient sample comprising reagents in separate containers, one of the reagents being a conjugate of a carrier containing a polymer having either a reactive thiol or amino group with a compound of the formula:

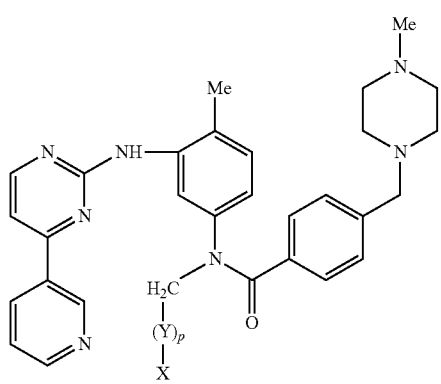

IV or its pharmacologically active salts;
wherein Y is an organic spacing group;
X is a terminal functional group capable of binding to said carrier through said amino or thiol group and;
p is an integer from 0 to 1;
and a second reagent in a separate container being an antibody which binds selectively to imatinib and its pharmacologically active salts without having any substantial cross-reactivity with the pharmacologically inactive metabolites of imatinib.

7. The kit of claim 6, wherein said conjugate is present in a predetermined amount in said first container.

8. The kit of claim 7, wherein said kit is used to determine the amount of imatinib and its pharmacologically active salts in said sample.

9. The kit of claim 8, wherein, said antibody is generated from an immunogenic carrier containing a polymer having either a reactive thiol or amino group linked to a compound of the formula:

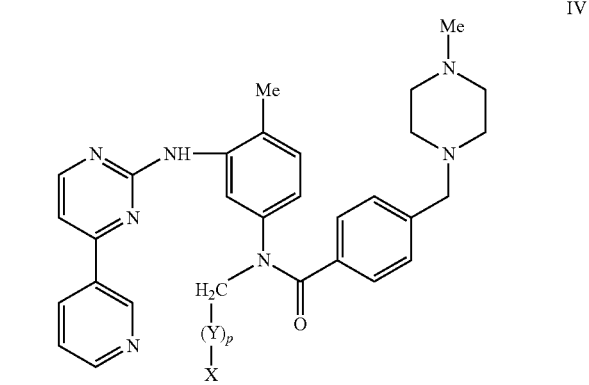

IV or its pharmacologically active salts;
wherein Y is an organic spacing group;
X is a terminal functional group capable of binding to said carrier through said amino or thiol group and;
p is an integer from 0 to 1.

* * * * *